United States Patent
Barthelemy et al.

(10) Patent No.: US 6,309,665 B2
(45) Date of Patent: Oct. 30, 2001

(54) COMPOSITION WITH SUSTAINED RELEASE OF ACTIVE PRINCIPLE, CAPABLE OF FORMING A MICROEMULSION

(75) Inventors: Philippe Barthelemy, Mions; Hassan Benameur, Genas-Azieu, both of (FR)

(73) Assignee: Gattefosse S.A., Saint Priest (FR)

(*) Notice: Subject to any disclaimer, the term of this patent is extended or adjusted under 35 U.S.C. 154(b) by 0 days.

(21) Appl. No.: 09/775,782

(22) Filed: Feb. 2, 2001

Related U.S. Application Data

(63) Continuation of application No. PCT/FR99/10889, filed on Jul. 30, 1999.

(30) Foreign Application Priority Data

Aug. 7, 1998 (FR) .................................................. 98 10313

(51) Int. Cl.[7] ...................................................... A61K 9/66
(52) U.S. Cl. ........................ 424/455; 424/484; 424/487; 424/488
(58) Field of Search .................... 424/400, 451, 424/455, 456, 457, 463; 514/937, 938, 944, 962, 963, 964, 965

(56) References Cited

U.S. PATENT DOCUMENTS

| | | | |
|---|---|---|---|
| 5,206,219 | 4/1993 | Desai . | |
| 5,508,022 | * 4/1996 | Clement et al. | 424/43 |
| 5,993,858 | * 11/1999 | Crison et al. | 424/490 |
| 6,054,136 | * 4/2000 | Farah et al. | 424/400 |

FOREIGN PATENT DOCUMENTS

| | | | |
|---|---|---|---|
| 0 222 614 A1 | 11/1986 | (EP) . | |
| 0 806 202 A1 | 12/1997 | (EP) . | |
| WO-95/24893-A1 | * 9/1995 | (GB) | A61K/9/48 |
| WO 95/08983 | 4/1995 | (WO) . | |
| WO 96/21439 | 7/1996 | (WO) . | |
| WO 99/12528 | 3/1999 | (WO) . | |

* cited by examiner

Primary Examiner—Thorman K. Page
Assistant Examiner—Charesse L. Evans
(74) Attorney, Agent, or Firm—Heslin, Rothenberg Farley & Mesiti P.C.

(57) ABSTRACT

The invention concerns a composition comprising a microemulsion forming system by contact with a hydrophilic phase brought, after ingestion, by the physiological fluid, said microemulsion forming system comprising: at least an active principle; a lipophilic phase; a surfactant (TA); a co-surfactant (CoTA). The invention is characterized in that said composition further comprises an inert polymeric matrix which cannot be ionised at physiological pH, dispersed in the microemulsion forming system before ingestion, said polymeric matrix being capable, after ingestion, of forming on contacting the physiological fluid, a gelled polymeric matrix enabling to release by diffusion, in continuous and prolonged manner the already microemulsified active principle.

20 Claims, 2 Drawing Sheets

COMPOSITION WITH SUSTAINED RELEASE OF ACTIVE PRINCIPLE, CAPABLE OF FORMING A MICROEMULSION

CROSS REFERENCE TO RELATED APPLICATIONS

This application is a continuation of copending PCT application PCT/FR 99/10889, filed Jul. 30, 1999, designating the United States and claiming priority from French application 98.10313, filed Aug. 7, 1998. The priorities of both applications are claimed herein, and the entire disclosures of both are incorporated herein by reference.

The invention relates to a composition with sustained release of active principle which can be administered orally in particular, for pharmaceutical or cosmetic use, which is capable of forming a microemulsion with an external hydrophilic phase, for example physiological fluid or water, while at the same time gradually releasing the active agent it contains in situ. The invention also relates to the process for manufacturing the said composition.

As is known, a microemulsion is a homogeneous, fluid, stable solution consisting of four major constituents, a hydrophilic phase, a lipophilic phase, at least one surfactant (SA) and at least one co-surfactant, respectively. Microemulsions are distinguished from emulsions and micellar solutions in particular by the size of the droplets of which they are formed. Specifically, the droplet size of a microemulsion is between 10 and 200 nanometres (nm) whereas it is less than 10 nm for a micellar solution and greater than 200 nm for an emulsion. Moreover, in contrast with emulsions, which are unstable, microemulsions, which necessarily comprise a co-surfactant, are stable. Furthermore, a microemulsion is characterized by its more or less pronounced transparency due to the proportion of reflected light transmitted by a light beam, the intensity of the light beam which is passed through being less than that of the incident beam. Since the reflected light is richer in blue and violet radiation, finely dispersed microemulsions have a bluish appearance. This is the so-called Tyndall effect described in particular in the book "Emulsions, micro-émulsions, emulsions multiples [Emulsions, microemulsions and multiple emulsions]" by Jean Poré.

In document EP-A-0 670 715, the Applicant disclosed a composition formed of a vector system of self-microemulsifiable active agent known by the expression SMEDDS®, a trademark registered by the Applicant, meaning Self Micro Emulsifying Drug Delivery System. These systems are disclosed at length in the abovementioned document and essentially comprise:

an active agent, a lipophilic phase consisting of a mixture of mono-, di- and triglycerides and of $C_8$–$C_{18}$ fatty acids and of polyethylene glycol monoesters and diesters with a hydrophilic/lipophilic balance (HLB) of less than 16;

a glyceride-based surfactant (SA) with an HLB of less than 16, chosen from the group comprising saturated $C_8$–$C_{10}$ polyglycosylated glycerides and oleic esters of polyglycerol;

a co-surfactant (CoSA) chosen from the group comprising lauric esters of propylene glycol, oleic esters of polyglycerol, ethyl diglycol and polyethylene glycol;

the SA-CoSA ratio being between 0.5 and 6.

Certain products sold by the Applicant, consisting of saturated and/or unsaturated fatty acids and of esters of these fatty acids, may be used as lipophilic phase, surfactant and co-surfactant, such as, for example, the combination of Gelucire 44/14, Labrafac CM10 and Lauroglycol, respectively, disclosed in Examples 1 and 2 of the abovementioned document.

The SMEDDS®s may be in solid or liquid form at room temperature, depending on the actual nature of the fatty substances of which they are composed. Thus, if at least one of the fatty substances constituting the SMEDDS® has a melting point which is greater than room temperature (about 25° C.), then the SMEDDS® will be semi-solid at room temperature. On the other hand, if at least one fatty substance constituting the SMEDDS® has a melting point of less than about 25° C., then the SMEDDS® is liquid at room temperature.

Consequently, the SMEDDS®s may be incorporated into gel capsules in liquid form, optionally while warm, and then, depending on the nature of their constituents, remain liquid or become semi-solid at room temperature.

Due to the formation of the microemulsion in situ, SMEDDS®s make it possible to dissolve the active principle and consequently to increase the bioavailability of the microemulsified active agent(s) they convey. However, the formation of the microemulsion gives the composition properties of immediate release of microemulsified active agent.

In other words, the problem which the invention proposes to solve is that of providing a composition of the SMEDDS® type which is capable of gradually releasing the active agent(s) it conveys, and of doing so whatever the consistency, solid or liquid, of the SMEDDS® at room temperature.

To solve this problem, the invention proposes a composition with sustained release of the active principle, for pharmaceutical or cosmetic use, which is intended to be ingested, comprising a system which is self-microemulsifying on contact with a hydrophilic phase provided, after ingestion, by the physiological fluid, the said self-microemulsifying system comprising:

at least one active agent, a lipophilic phase consisting of a mixture of mono-, di- and triglycerides and of $C_8$–$C_{18}$ fatty acids and of polyethylene glycol monoesters and diesters with a hydrophilic/lipophilic balance (HLB) of less than 16;

a glyceride-based surfactant (SA) with an HLB of less than 16, chosen from the group comprising saturated $C_8$–$C_{10}$ polyglycosylated glycerides and oleic esters of polyglycerol;

a co-surfactant (CoSA) chosen from the group comprising fatty acid esters of propylene glycol, oleic esters of polyglycerol, ethyldiglycol and polyethylene glycol;

the SA-CoSA ratio being between 0.5 and 6.

The composition of the invention is characterized in that it also comprises an inert polymer matrix which is not ionizable at physiological pH, dispersed in the self-microemulsifying system before ingestion, the said polymer matrix being capable, after ingestion, of forming, in contact with physiological fluid, a gelled polymer matrix making it possible to release the thus microemulsified active agent in a continuous and sustained manner by diffusion.

In the description hereinbelow and in the claims, the expression "microemulsified active agent" denotes the active agent dissolved in the microemulsion, i.e. in its hydrophobic zone.

Similarly, the expression "physiological fluid" denotes the physiological medium in vivo, as is found after ingestion of the composition and the pH of which will vary as a function of the state of the gastrointestinal tract.

However, at the experimental stage, i.e. without ingestion of the composition, the physiological fluid is replaced with water or a physiological medium reconstituted in vitro. In this case, the microemulsion will be formed on simple contact with the aqueous phase.

Hereinbelow in the description and in the claims, the expression "polyglycosylated glycerides" denotes a mixture of mono-, di- and triglycerides and of polyethylene glycol (PEG) mono- and diesters with a molecular weight preferably of between 200 and 600, optionally of glycerol and of free PEG, the HLB value of which is controlled by the chain length of the PEG and the melting point of which is controlled by the chain length of the fatty acids, of the PEG and of the degrees of saturation of the fatty chains, and thus of the starting oil.

Similarly, the expression "$C_8$ to $C_{18}$ fatty acids", also written $C_8$–$C_{18}$ fatty acids, denotes mixtures in significant and variable proportions of caprylic ($C_8$) acid, capric ($C_{10}$) acid, lauric ($C_{12}$) acid, myristic ($C_{14}$) acid, palmitic ($C_{16}$) acid and stearic ($C_{18}$) acid, when these acids are saturated, and the corresponding $C_8$–$C_{18}$ unsaturated acids.

It is recalled that the proportions of these fatty acids may vary as a function of the starting oils.

In one preferred embodiment of the invention, the co-surfactant is chosen from the group comprising lauric esters of propylene glycol, capric esters of propylene glycol and palmitic esters of propylene glycol.

In other words, the invention consists in incorporating an inert polymer matrix into a self-microemulsifying system. The said self-microemulsifying system thus forms a microemulsion after ingestion, on contact with physiological fluid, thus making it possible, by diffusion through the matrix which has thus become gelled on contact with the physiological fluid, to gradually, continuously and uniformly release the microemulsified active agent(s).

In practice, when the composition of the invention is formulated as gel capsules, after ingestion, the gel capsule dissolves on contact with the digestive fluids, resulting in parallel in the formation of a small fraction of microemulsion, since the water gradually comes into contact with the SMEDDS®. The result of this is that a small proportion of the active principle is thus microemulsified, and the microemulsified active principle is then released.

Concomitantly, the polymer gradually becomes hydrated, then gels, resulting in the formation of a viscous layer, the volume of which increases gradually to form a matrix from which the microemulsion is released by diffusion. The gelled barrier thus formed therefore counters the rapid release of the microemulsified active principle and, by controlling the penetration of water from the outside inwards, makes it possible gradually to release the said microemulsified active principle.

Moreover, when the SMEDDS® comprises fatty substances with an HLB value >10, it has been found, entirely surprisingly, that the polymer matrix is gelled only after ingestion, i.e. in contact with physiological fluid, whereas it might have been expected that the gelation would have taken place before ingestion merely on contact with the constituents of the SMEDDS®, the very high HLB value of which (>10) would have resulted in salvation of the polymer, and thus have led to the formation of a gel.

Furthermore, it was not obvious that the rate of release of active agent would not change as a function of the hydrodynamic conditions, i.e. as a function of the intestinal motility, in particular by erosion of the matrix, as occurs for monolithic systems. On the contrary, the composition according to the invention has the advantage of being independent of the hydrodynamic conditions, since the matrix on contact with physiological fluid swells and forms a continuous network, allowing release of the micelles forming the microemulsion.

In a first embodiment of the invention, in order for the polymer matrix to form a hydrated network and thus a gel on contact with physiological fluid, the polymer matrix is chosen from the group comprising cellulose polymers.

According to this embodiment, the polymer matrix has a molecular weight of less than one million.

For a molecular weight of greater than one million, the viscosity of the composition is too high and the release of the SMEDDS® is improved.

The molecular weight of the polymer matrix is advantageously between 80,000 and 800,000.

In a second embodiment of the invention, the polymer matrix is chosen from the group comprising acrylic polymers. Any acrylic polymer capable of swelling on contact with an aqueous phase may be suitable.

In a third embodiment of the invention, the polymer matrix is chosen from the group comprising non-cellulose polysaccharides, for example gums.

When it is desired to incorporate a hydrophobic active agent into the SMEDDS®, a hydrophilic polymer matrix chosen from the group comprising hydroxypropylcellulose, hydroxypropylmethylcellulose and methylcellulose, alone or as a mixture, is used.

Similarly, when it is desired to incorporate a hydrophilic active agent into the SMEDDS®, a hydrophobic polymer matrix such as ethylcellulose is used.

The composition of the invention thus makes it possible to use hydrophilic active agents independently of their water solubility, since the release of the active agent does not take place as a function of its water solubility, but by diffusion of micelles, the active agent being presented beforehand in a form of SMEDDS®.

To bring about gelation of the polymer matrix on contact with physiological fluid, while at the same time ensuring the formation of the microemulsion, the inert polymer matrix represents from 0.5% to 40% relative to the weight of the total composition.

For a concentration of less than 0.5%, no gelation of the matrix is observed on contact with physiological fluid. In contrast, for a matrix concentration of greater than 40%, the solution becomes too viscous.

The concentration of polymer matrix is advantageously between 5% and 25% relative to the total weight of the composition.

The invention also relates to the process for manufacturing the composition.

According to this process:
a self-microemulsifying system is first prepared by mixing, if necessary while heating, with stirring, the active agent, the lipophilic phase, the surfactant and the co-surfactant;
the polymer matrix in powder form is then gradually dispersed, while still stirring, in the said self-microemulsifying system.

The composition of the invention, which is in liquid or semi-solid form at room temperature depending on the nature of the constituents of the SMEDDS®, will be formulated in the form of gel capsules.

In this case, these capsules will be filled with the composition of the invention in liquid form, optionally preheated, which liquid, during cooling and depending on the composition of the SMEDDS , may solidify at room temperature.

The invention thus also relates to the sustained-release gel capsule incorporating the SMEDDS® described above.

The invention and the advantages following therefrom will emerge more clearly from the embodiment below in support of the attached figures.

EXAMPLE 1

Figure 1A:
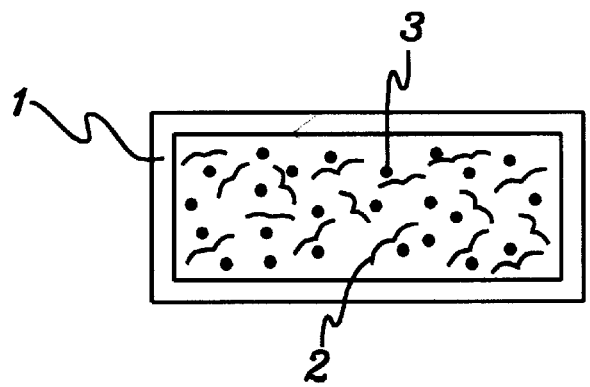
FIG. 1 is a diagrammatic representation of the system for releasing the active agent from the composition of the invention.
Figure 1B:
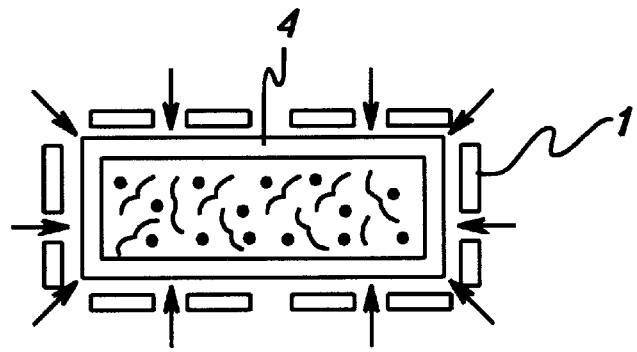

As already stated, FIG. 1 shows the functioning of the polymer matrix dispersed in a formulation of SMEDDS® type, the composition obtained being in the form of a gel capsule.

FIG. 1a represents a gel capsule (1) containing a polymer matrix (2) distributed homogeneously and in dry form in the bulk and a self-microemulsifying system (3) or SMEDDS®.

As shown in FIG. 2a, on contact with the hydrophilic phase, i.e. physiological fluid, the gel capsule (1) is dissolved, which allows the physiological fluid to enter the mixture of polymer and SMEDDS®.

On contact with water, the polymer matrix gradually forms by structuring a gelled barrier (4).

Figure 1C:
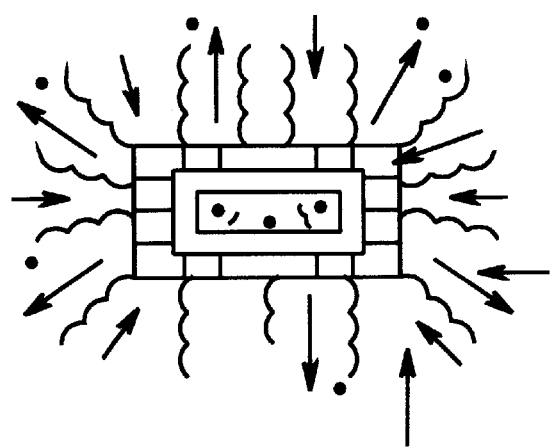

As shown in FIG. 1c, the polymer matrix gradually becomes destructured, thus allowing the SMEDDS® to be released slowly.

EXAMPLE 2

The test below was carried out in a laboratory using water as physiological medium.

Manufacture of the Composition of the Invention in the Form of a Gel Capsule

In this example, a SMEDDS® is prepared, the composition of which is as follows:

| | | |
|---|---|---|
| surfactant | Labrasol | 43.40% |
| co-surfactant | Plurololeic | 14.40% |
| lipophilic phase | Labrafil WL2609BS | 38.40% |
| active principle | Indomethacin | 4% |

In a known manner, the constituents of the SMEDDS® are mixed together at room temperature with stirring of between 60 and 100 rpm.

The polymer matrix consisting of hydroxypropylmethylcellulose (HPMC) representing 20% of the final composition is then gradually dispersed, while still stirring.

A liquid preparation is obtained which is then formulated in the form of gel capsules.

Dissolution Curves

Figure 2:
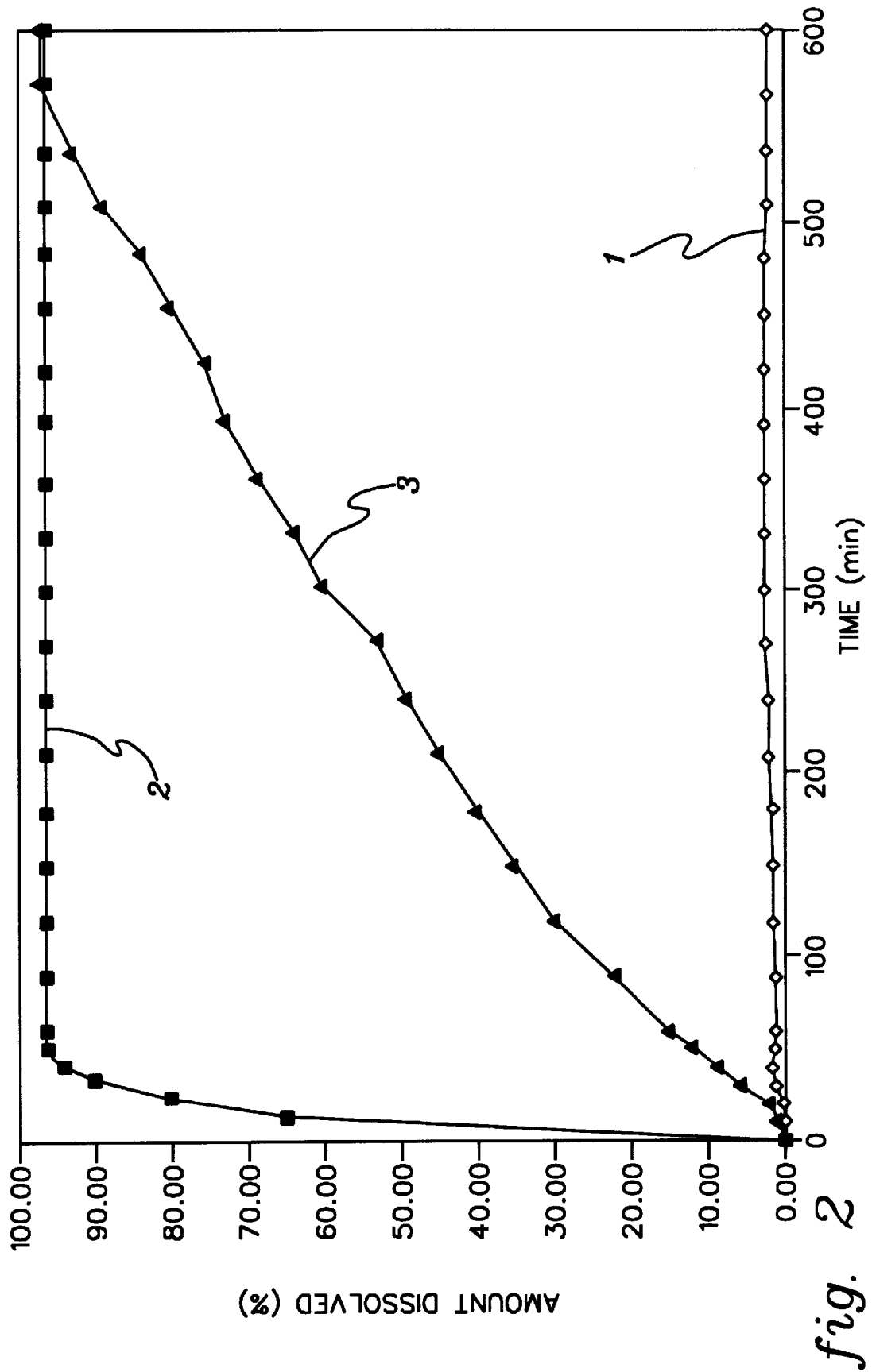
FIG. 2 is a representation of the dissolution curves of indomethacin at pH 1.2 for indomethacin alone, indomethacin formulated in the form of SMEDDS® as disclosed in document EP-A-0 670 715 and indomethacin formulated in the form of sustained-release SMEDDS® as disclosed in the present invention.

FIG. 2 represents the dissolution curves for indomethacin when the active agent is alone (curve 1), in the form of immediate-release SMEDDS® (curve 2), or in the form of sustained-release SMEDDS® according to the invention (curve 3).

As shown in this figure, the indomethacin, which is known to be insoluble at acidic pH (curve 3), can be made fully available when it is incorporated in a SMEDDS® (curves 1 and 2).

As shown in curve 2, the composition of the invention has sustained-release characteristics, despite the fact that the SMEDDS® is in liquid form at room temperature.

Characterization of the Microemulsion Formed by the Composition of the Invention Tyndall Effect The microemulsion obtained in vitro has a bluish appearance which corresponds to the Tyndall effect.

Size of the Droplets Forming the Microemulsion

The size of the droplets of the microemulsion obtained in vitro when the composition of the invention is placed in contact with an aqueous phase was measured by photon correlation spectroscopy.

The mean droplet size obtained is 25 nanometres.

The advantages of the invention clearly emerge from the description above.

The possibility of incorporating SMEDDS®s into sustained-release forms will be noted in particular, thus making it possible to increase the bioavailability of the active agent.

It will also be noted, entirely surprisingly, that the composition of the invention has a structure such that it allows gradual release of the active principle in viva, even if the SMEDDS® is in liquid form at room temperature.

What is claimed is:

1. Composition intended to be ingested, comprising a system which is self-microemulsifying on contact with a hydrophilic phase provided, after ingestion, by physiological fluid, the said self-microemulsifying system comprising:
   at least one active agent;
   a lipophilic phase consisting of a mixture of mono-, di- and triglycerides and of $C_8$–$C_{10}$ fatty acids and of polyethylene glycol monoesters and diesters with a hydrophilic/lipophilic balance (HLB) of less than 16;
   a glyceride-based surfactant (SA) with an HLB of less than 16, selected from the group consisting of saturated $C_8$–$C_{10}$ polyglycosylated glycerides and oleic esters of polyglycerol;
   a co-surfactant (CoSA) selected from the group consisting of fatty acid esters of propylene glycol, oleic esters of polyglycerol, and ethyl diglycol;
   an inert polymer matrix, representing from 0.5% to 40% relative to the weight of the total composition, which is not ionizable at physiological pH, dispersed in the self-microemulsifying system before ingestion, the said polymer matrix being capable, after ingestion, of forming, in contact with physiological fluid, a gelled polymer matrix making it possible to release the thus microemulsified active agent in a continuous and sustained manner by diffusion, and wherein the surfactant—co-surfactant ratio is between 0.5 and 6.

2. Composition according to claim 1, wherein the co-surfactant is a fatty ester of propylene glycol selected from the group consisting of lauric esters of propylene glycol, capric esters of propylene glycol and palmitic esters of propylene glycol.

3. Composition according to claim 1, wherein the polymer matrix comprises one or more cellulose polymers.

4. Composition according to claim 3, wherein the molecular weight of the polymer matrix is less than one million.

5. Composition according to claim 4, wherein the molecular weight of the polymer matrix is between 80,000 and 800,000.

6. Composition according to claim 1, wherein the polymer matrix is hydrophilic and selected from the group consisting of hydroxypropylcellulose, hydroxypropylmethylcellulose, methylcellulose, and mixtures thereof.

7. Composition according to claim 1, wherein the polymer matrix is hydrophobic and comprises ethylcellulose.

8. Composition according to claim 1, wherein the polymer matrix comprises one or more acrylic polymers which are capable of swelling on contact with an aqueous phase.

9. Composition according to claim 1, wherein the polymer matrix comprises one or more non-cellulose polysaccharides.

10. Composition according to claim 1, wherein the inert polymer matrix represents from 5% to 25% relative to the weight of the total composition.

11. Process for manufacturing the composition of claim 1, in which:

a self-microemulsifying system is first prepared by mixing, if necessary while heating, with stirring, the active agent, a lipophilic phase, a surfactant and a co-surfactant;

the polymer matrix in powder form is then gradually dispersed, while still stirring, in the said self-microemulsifying system.

12. Gel capsule incorporating the composition of claim 1.
13. Gel capsule incorporating the composition of claim 2.
14. Gel capsule incorporating the composition of claim 3.
15. Gel capsule incorporating the composition of claim 4.
16. Gel capsule incorporating the composition of claim 5.
17. Gel capsule incorporating the composition of claim 6.
18. Gel capsule incorporating the composition of claim 7.
19. Gel capsule incorporating the composition of claim 8.
20. Gel capsule incorporating the composition of claim 9.

\* \* \* \* \*